United States Patent [19]

Torday

[11] Patent Number: 5,980,470
[45] Date of Patent: Nov. 9, 1999

[54] ESTRIOL MONITORING OF MATERNAL BLOOD FOR ANTENATAL STEROID ACCELERATION OF FETAL LUNG MATURATION

[75] Inventor: John S. Torday, Baltimore, Md.

[73] Assignee: ProBiotix, Inc., Baltimore, Md.

[21] Appl. No.: 09/030,905

[22] Filed: Feb. 26, 1998

Related U.S. Application Data

[60] Provisional application No. 60/039,443, Feb. 26, 1997.

[51] Int. Cl.$^6$ ........................................................ A61B 5/00
[52] U.S. Cl. ............................................................ 600/584
[58] Field of Search .................................... 600/573, 584; 206/569, 570, 571

[56] References Cited

U.S. PATENT DOCUMENTS

| 4,472,357 | 9/1984 | Levy et al. ............................. 600/584 |
| 5,048,539 | 9/1991 | Schindele .............................. 600/584 |

OTHER PUBLICATIONS

Kauppila, Antti, et al., "Effect of Dexamethasone on Blood Levels of ACTH, Cortisol, Progesterone, Estriol and Estriol during Late Pregnancy," Int. J. Gynaecol Obstet 14:177–181, 1976.

Friedrich, F., et al., "Betamethasontest zur Diagnose der Plazentainsuffizienz," Symposium der Deutschen Gesellschaft fur Endokrinologie, Feb. 24–27/1982.

Kappy, Kenneth A., et al., "Betamethasone and the Hormonal Status of the Pregnant Diabetic Woman," Int J Gynaecol Obstet 17:465–466, 1980.

Whitt, Gerald G., et al., "A Comparison of Two Glucocorticoid Regimens for Acceleration of Fetal Lung Maturation in Premature Labor," Am. J. Obstet. Gynecol., vol. 124, No. 5, 479–482, 1976.

Kjer, J.J., et al., "Serum Estriol Level during Treatment with Betamethasone in the Last Trimester of Human Pregnancy," Acta Obstet Gynecol Scand, 62:307–309, 1983.

*Primary Examiner*—Max Hindenburg
*Attorney, Agent, or Firm*—James Creighton Wray; Meera P. Narasimhan

[57] ABSTRACT

Maternal blood unconjugated estriol is used to determine whether steroid treatment has or has not effectively accelerated fetal lung maturation and reduced the risk of RDS. A blood sample is obtained from the mother prior to treating her with steroids and again 24 hours later. The blood cells are separated from the serum and the serum is analyzed for unconjugated estriol concentration in the two blood samples obtained. If the percent change in the estriol concentration of the mother's blood decreases by a significant percentage over the 24 hour period from the start of the steroid treatment, the infant will not develop RDS. If the percent change in the estriol concentration of the mother's blood does not decrease by a significant percentage over the 24 hour period from the start of the steroid treatment, the infant will be at the same risk of RDS as it would have been without the steroid treatment. The information obtained from this test is used to make decisions regarding further treatment.

21 Claims, 2 Drawing Sheets

ESTRIOL MONITORING OF MATERNAL BLOOD FOR ANTENATAL STEROID ACCELERATION OF FETAL LUNG MATURATION

This application claims the benefit of U.S. Provisional Application No. 60/039,443, filed Feb. 26, 1997.

BACKGROUND OF THE INVENTION

The present invention relates to prenatal testing and treatment, and in particular to prenatal testing and treatment relating to respiratory distress syndrome encountered in newborn premature human infants.

Respiratory distress syndrome (RDS) is a condition often suffered in infants delivered prematurely, i.e., before the normal 37 weeks gestation period. Women at risk for premature delivery have been treated with steroids such as betamethasone, dexamethasone or other known glucocorticoids, in order to accelerate fetal lung maturation. However, this therapy has only been partially effective in the prevention of RDS. It is known that fetal adrenal androgens block steroid-stimulated fetal lung maturation. Accordingly, a need exists for detecting the interference by fetal adrenal androgens in the prenatal treatment of babies at risk of premature birth in order to prevent occurrences of RDS.

One of the difficulties with prior art steroid treatment is that there is no method of determining whether the fetus has responded to steroid treatment before birth. There have been reports of antenatal steroid treatment for acceleration of fetal lung maturation and its inhibition of maternal blood estriol. There are also reports that decreasing maternal urinary or blood estriol is indicative of fetal illness. It would be desirable to be able to determine whether the fetus has responded to steroid treatment before birth so that appropriate steps can be taken in the treatment of the mother in the final stages of pregnancy.

SUMMARY OF THE INVENTION

Maternal blood unconjugated estriol is used to determine whether steroid treatment has or has not effectively accelerated fetal lung maturation and reduced the risk of RDS. A blood sample is obtained from the mother prior to treating her with steroids and again 24 hours later. The blood cells are separated from the serum and the serum is analyzed for unconjugated estriol concentration in the two blood samples obtained. If the percent change in the estriol concentration of the mother's blood decreases by a significant percentage over the 24 hour period from the start of the steroid treatment, the infant will not develop RDS. If the percent change in the estriol concentration of the mother's blood does not decrease by a significant percentage over the 24 hour period from the start of the steroid treatment, the infant will be at the same risk of RDS as it would have been without the steroid treatment. The information obtained from this test is used to make decisions regarding further treatment.

These and further and other objects and features of the invention are apparent in the disclosure, which includes the above and ongoing written specification, with the claims and the drawings.

DESCRIPTION OF THE PREFERRED EMBODIMENTS

Figure 1:
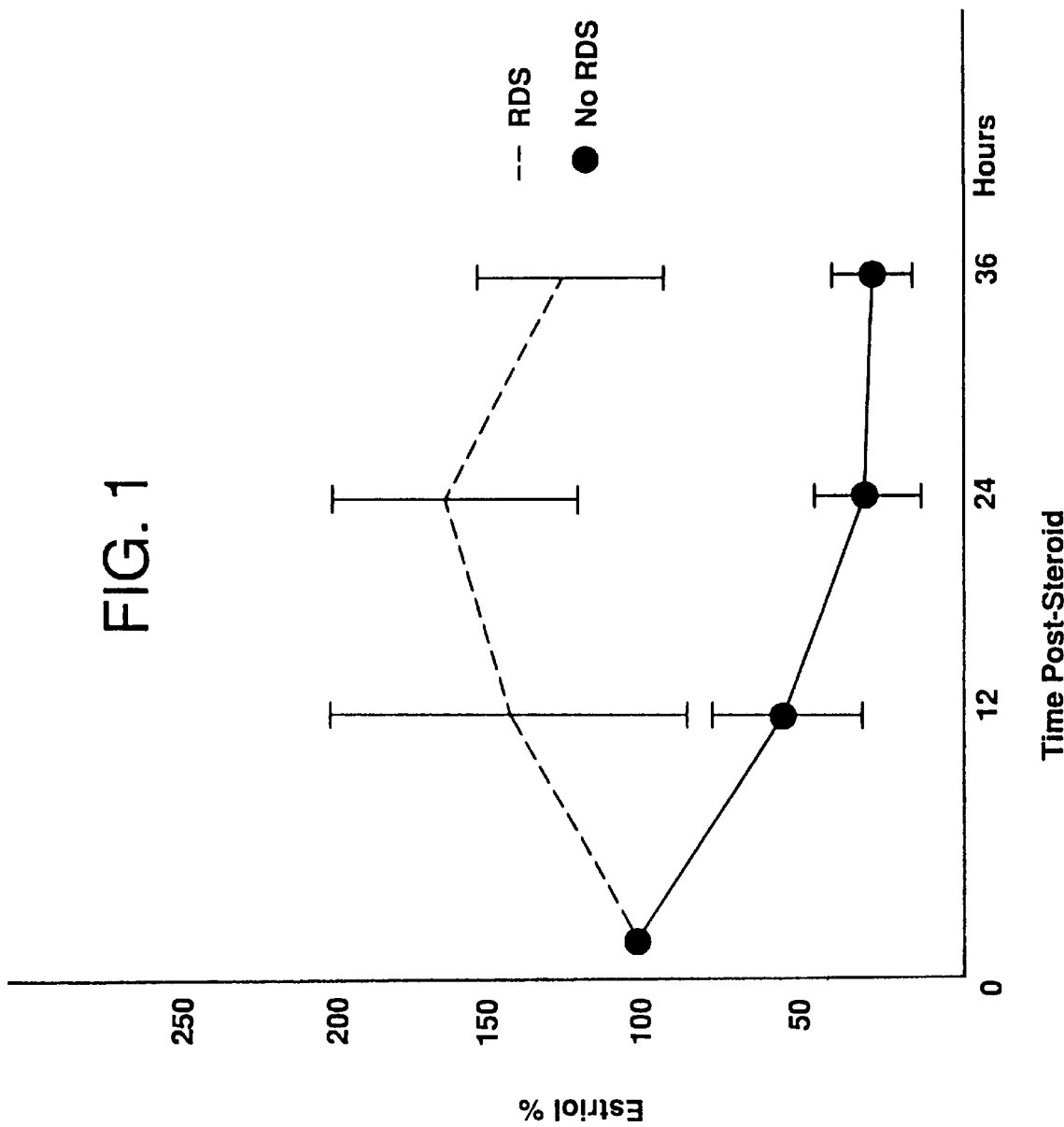
FIG. 1 is a graph of the percent change in maternal blood unconjugated estriol versus time duration post-steroid treatment.

In this invention, maternal blood unconjugated estriol is shown to predict whether maternal antenatal steroid treatment accelerates fetal lung maturation alleviating the risk of respiratory distress syndrome. The inventor has discovered a relationship between antenatal steroid treatment not inhibiting maternal blood estriol and lack of the steroid effect on acceleration of fetal lung maturation. The inventor has discovered and demonstrated that fetal androgens produced by the testes block the acceleration of fetal lung maturation by steroids. Also, fetal androgens produced by the adrenal gland block the acceleration of fetal lung maturation by steroids. These findings are central to the invention since the failure of steroids to inhibit the production of androgen by the fetal adrenal gland results in androgen inhibitions of steroid acceleration of fetal lung maturation and failure to inhibit maternal blood unconjugated estriol. This biological interrelationship also holds true for the effect of antenatal steroid treatment on the fetal brain, gastrointestinal tract, heart, retina and skin. Therefore, maternal blood unconjugated estriol will predict whether maternal antenatal steroid treatment on the fetal brain, gastrointestinal tract, heart, retina and skin. Therefore, maternal blood unconjugated estriol will predict whether maternal antenatal steroid treatment reduces the risk of intraventricular hemorrhage, necrotizing enterocolitis, patent ductus arteriosus, retrolental fibroplasia and dehydration. Since these are the principle risks of premature birth, maternal blood estriol will predict fetal maturity in women receiving antenatal steroids.

In the preferred procedure, a blood sample of 1–5 milliliters is obtained by ordinary venipuncture from the mother. She is then treated with steroids of the general type known as glucocorticoids. However, the present and preferred steroids are betamethasone and dexamethasone. The recommended treatment regimen is 12 milligrams for 24 hours for 2 consecutive days. The drug is administered intramuscularly with a hypodermic needle to the mother and the drug crosses the placenta to the fetus. Twenty four hours after the initial steroid treatment, another blood sample is taken from the mother for analysis.

The blood analysis of both the initial blood sample and the sample taken after 24 hours is as follows. The blood cells are separated from the serum and the serum is analyzed for unconjugated estriol concentration in the two blood samples obtained. Unconjugated estriol can be measured either calorimetrically, by radioimmunoassay, or by enzyme linked immunosorbent assay. If the percent change in estriol concentration of the mother's blood decreases by 40% or more over the 24 hour period from the start of the steroid treatment, the infant will not develop respiratory distress syndrome. The percent change is measured by the formula:100×[estriol concentration at time zero—estriol concentration at 24 hours]:estriol concentration at time zero. If the percent change in estriol content of the mother's blood decreases less than 40% over the 24 hour period from the start of steroid treatment (i.e., time zero), the infant is at the same risk of developing respiratory distress syndrome as it would have been without the steroid treatment. The risk of developing respiratory distress syndrome is dependent on the gestational age of the fetus at the time of birth and it ranges from 100% at 24 weeks gestation to 0% at 37 weeks gestation, decreasing linearly in between. If the percent change in the estriol content of the mother's blood decreases less than 40% over the 24 hour period from the start of the steroid treatment, the mother may be retreated with steroids or other drugs as indicated, and re-evaluated for maternal blood unconjugated estriol as previously described.

As previously noted, unconjugated estriol can be measured colorimetrically, by radioimmunoassay or by enzyme linked immunosorbent assay. Enzyme linked immunosorbent assay is the preferred technique because it can be done rapidly, inexpensively and can be performed by nontechnically trained individuals. The calorimetric and radioimmunoassay methods are time-consuming, labor intensive and must be done by highly trained and skilled personnel working in a laboratory setting, rendering these tests more expensive, less accessible, and therefore less—or non-utilizable by the practitioner.

CASE EXAMPLES

Example 1

A clinical case in which the infant did not respond to the steroid treatment. Patient DJK—a twin pregnancy admitted to the Labor and Delivery service of University Hospital, Baltimore, Md. on Jun. 14, 1995 for preterm labor at 30 weeks gestation. The patient was initially treated with labor-stopping drugs and then was started on betamethasone to reduce the risk of respiratory distress syndrome if the infants were delivered. Informed Consent was obtained from the mother before obtaining blood samples for estriol determinations. Two infants, one male and one female, were delivered by Caesarean section at 1:54 a.m. on Jun. 17, 1995 at 890 grams and 1150 grams body weight, respectively. Both infants were diagnosed with sever respiratory distress syndrome. The mother's blood unconjugated estriol was unchanged between the start of the steroid treatment and 24 hours after the initiation of the steroid treatment.

Example 2

A clinical case in which the infant responded to the steroid treatment. Patient JW—singleton pregnancy admitted to Labor and Delivery service, University Hospital, Baltimore, Md. on Jun. 20, 1995 for preterm labor at 28 weeks gestation. The patient was treated with a full course of betamethasone. Informed Consent was obtained from the mother before obtaining blood samples for estriol determinations. An 875 gram female infant was delivered by spontaneous vaginal delivery at 5:04 p.m. 6 days later on Jun. 27, 1995. The infant had no symptoms of respiratory distress syndrome. The mother's blood unconjugated estriol decreased by 755 between the start of steroid treatment and 24 hours after initiation of steroid treatment.

Summary of Results From Case Studies

Preliminary results of the experimental use of maternal blood unconjugated estriol to determine the efficacy of antenatal steroids for reduction of risk of respiratory distress syndrome. Ninety-three pregnant women in premature labor at less than or equal to 30 weeks gestation on admission to Labor and Delivery service, University Hospital, Baltimore, Maryland being treated with steroids to reduce the risk of neonatal respiratory distress syndrome were enrolled in the study after obtaining Informed Consent. In all cases maternal blood samples were obtained by venipuncture at the start of the steroid treatment and again at 24 hours after the start of steroid treatment in order to determine the concentrations of maternal blood unconjugated estriol. In no case was the estriol value used for clinical management of these patients. Fifty-seven of the 93 enrolled patients were eligible for the study, i.e., 2-day steroid treatment prior to delivery, and delivered within 7–10 days from the initiation of the steroid treatment. For the infants to qualify for the study, they had to be free of pneumonia and asphyxia at the time of birth. Among these 57 qualified cases, there were 40 infants without respiratory distress syndrome and 17 with documented respiratory distress syndrome. The maternal blood unconjugated estriol concentrations in the 40 infants without respiratory distress syndrome at birth decreased by 80+/−20 at 24 hours after the initiation of steroid treatment, the maternal blood unconjugated estriol concentrations in the 17 infants with respiratory distress syndrome at birth increased by 66+/−54% at 24 hours after the initiation of steroid treatment. The mean blood estriol concentration at the time of initiation of steroid treatment in the group that developed respiratory distress syndrome at the time of birth.

Based on these preliminary data, it can be concluded that the percent change in maternal blood unconjugated estriol among pregnant women less than or equal to 30 weeks gestation receiving steroids to reduce the risk of respiratory distress syndrome at birth.

The accompanying figure is a graph summarizing these results. The horizontal scale is the time duration post-steroid treatment in hours. The vertical scale is the percent estriol. The test results are shown in vertical bars with the average indicated at the center of each bar. The maximum divergence is seen at the 24 hour time duration. Accordingly, in the preferred test procedure, the second blood sample is taken at 24 hours after taking the first blood sample, which is taken just prior to the initiation of the steroid treatment.

Figure 2:
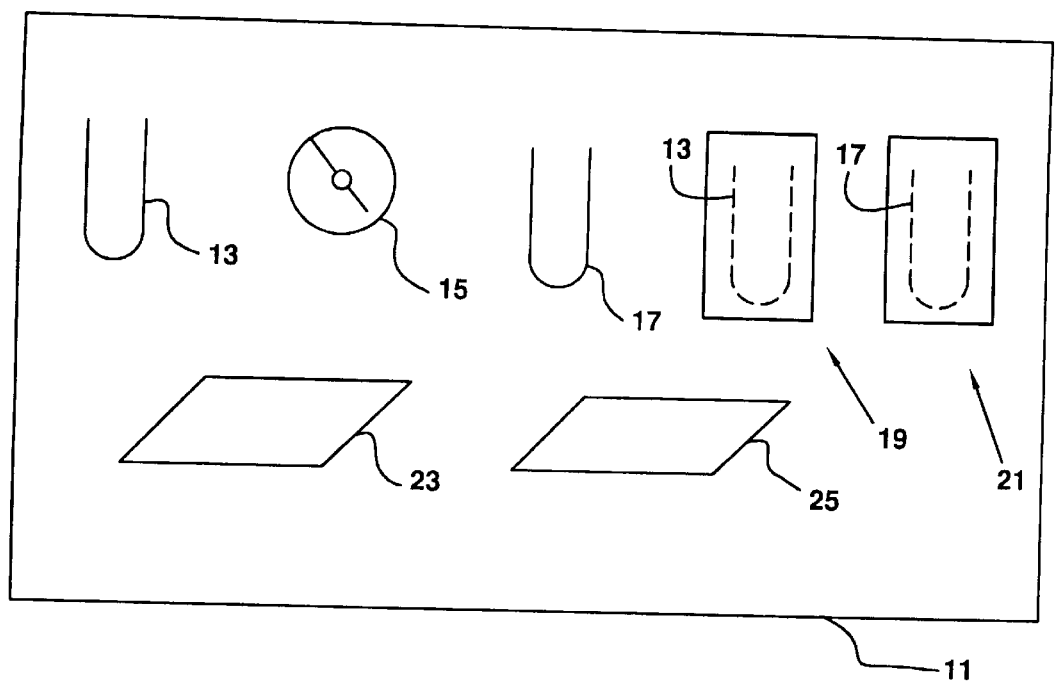
FIG. 2 is a kit for testing and predicting fetal response.
Figure 3:
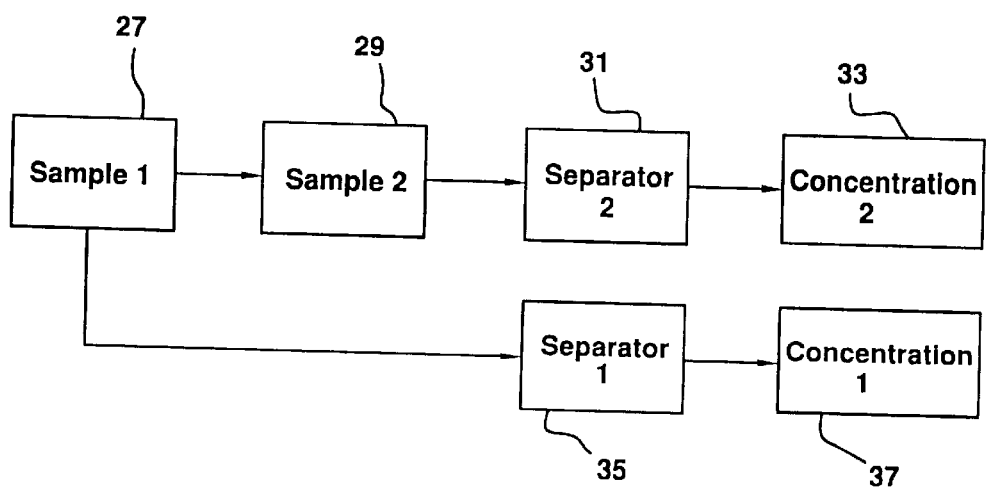
FIG. 3 is a schematic of the process for testing and predicting fetal response to steroid treatment.

A preferred embodiment is a kit 11, as shown in FIG. 2. The kit may contain two vials 13 and 17 for taking the first and second blood samples, a 24 hour timer 15 for alerting the user to when to take the second sample, two seperators 19 and 21 for separating the blood cells from the serum and two comparators 23 and 25 for measuring the unconjugated estriol concetrations. FIG. 3 details the steps involved in the process. First a user takes a first blood sample 27. The first sample then has the blood cells separated from the serum 35. Twenty-four hours after taking the first sample 27, the user takes a second sample 29. This sample is also then separated 31. Both samples 31 and 35 are then measured to determine their unconjugated estriol concentrations 33 and 37. The steroid treatment was effective if a concentration decrease greater than 40% was achieved. A concentration decrease of less than 40% indicates that the steroid treatment was ineffective.

While the invention has been described with reference to specific embodiments, modifications and variations of the invention may be constructed without departing from the scope of the invention, which is defined in the following claims.

I claim:

1. A method of testing for fetal response to steroid treatment before birth comprising withdrawing a first sample of blood from a mother, providing a steroid treatment to the mother, waiting several hours, withdrawing a second sample of blood from the mother, separating blood cells from first and second serums in the first and second samples, analyzing the first and second serums for unconjugated estriol concentrations, comparing the unconjugated estriol concentrations, observing percentage decrease of the unconjugated estriol concentrations in the first and second serums, and predicting successful fetal response to the steroid treatment upon observing the percentage decrease as significant.

2. The method of claim 1, wherein the predicting comprises predicting successful steroid treatment upon decrease of 40% or more in concentration.

3. The method of claim 1, further comprising adjusting the providing a steroid treatment according to the predicting of fetal response.

4. The method of claim 1, wherein providing the steroid treatment comprises providing maternal antenatal intramuscular injection of glucocorticoids.

5. The method of claim 4, wherein the glucocorticoids are selected from a group consisting of betamethasone and dexamethasone.

6. The method of claim 5, wherein providing the steroid treatment comprises providing doses of 12 mg for 24 hours for 2 consecutive days.

7. The method of claim 1, wherein the waiting several hours comprises waiting for about 24 hours.

8. The method of claim 1, wherein the fetal response comprises fetal response to maternal antenatal steroid treatment for accelerating fetal lung maturation and alleviating risk of respiratory distress syndrome.

9. The method of claim 1, wherein the fetal response comprises fetal response to maternal antenatal steroid treatment for reducing risk of intraventricular hemorrhage, necrotizing enterocolitis, patent ductus arteriosus, retrolental fibroplasia and dehydration.

10. The method of claim 1, wherein the analyzing comprises calorimetric analysis.

11. The method of claim 1, wherein the analyzing comprises radioimmunoassay analysis.

12. The method of claim 1, wherein the analyzing comprises enzyme linked immunosorbent assay analysis.

13. A method of testing for fetal response to steroid treatment comprising withdrawing a first maternal fluid sample, providing a steroid treatment, waiting a predetermined time, withdrawing a second maternal fluid sample, measuring for an hormone concentration in the first and second samples, comparing the hormone concentrations from the first and second samples, and predicting fetal effectiveness of the steroid treatment according to decrease in concentration of the hormone from the first sample to the second sample.

14. The method of claim 13, wherein the measuring is measuring for unconjugated estriol concentration.

15. The method of claim 13, wherein the withdrawing of first and second samples is withdrawing blood.

16. The method of claim 13, wherein the predicting effectiveness comprises predicting successful steroid treatment upon decrease of 40% or more in the concentration.

17. The method of claim 13, wherein the waiting comprises waiting for about 24 hours.

18. The method of claim 13, wherein the testing for fetal response comprises testing for fetal response to maternal antenatal steroid treatment for accelerating fetal lung maturation and alleviating risk of respiratory distress syndrome.

19. The method of claim 13, wherein the testing for fetal response comprises testing for fetal response to maternal antenatal steroid treatment for reducing risk of intraventricular hemorrhage, necrotizing enterocolitis, patent ductus arteriosus, retrolental fibroplasia and dehydration.

20. The method of claim 13, wherein the measuring is calorimetrically by enzyme linked immunosorbent assay analysis.

21. A kit for testing fetal response to steroid treatment, comprising a first vial for receiving a first maternal fluid sample, a second vial for receiving a second maternal fluid sample, measuring means for measuring concentration of a hormone in the first and second samples, and a comparator for comparing decrease in the concentration between the first sample and the second sample, wherein the fluid is blood and the hormone is unconjugated estriol, and further comprising a separator for separating cells from serum in the samples, and wherein the measuring means comprise means for calorimetrically measuring by enzyme linked immunosorbent assay a first concentration of unconjugated estriol in the second sample, and wherein the comparator comprises means for showing percentage decrease of the first and second concentrations.

* * * * *